United States Patent [19]

Schiefer et al.

[11] Patent Number: 4,771,176
[45] Date of Patent: Sep. 13, 1988

[54] METHOD FOR QUANTITATIVE ANALYSIS OF HYDROCARBON

[75] Inventors: Erich J. Schiefer, Selzthal; Wolfgang Schindler; Peter W. Krempl, both of Graz, all of Austria

[73] Assignee: Avl Gesellschaft für Verbrennungskraftmaschinen und Messtechnik m.b.H., Graz, Austria

[21] Appl. No.: 937,612

[22] Filed: Dec. 3, 1986

[30] Foreign Application Priority Data

Dec. 9, 1985 [AT] Austria .................. 3566/85

[51] Int. Cl.$^4$ ........................... G01J 3/42
[52] U.S. Cl. .................. 250/339; 250/340; 250/343
[58] Field of Search ......... 250/343, 344, 345, 346, 250/339

[56] References Cited

U.S. PATENT DOCUMENTS

| | | | |
|---|---|---|---|
| 3,932,754 | 1/1976 | Riedl et al. | 250/343 |
| 3,957,372 | 5/1976 | Jowett et al. | 250/345 |
| 3,998,557 | 12/1976 | Javan | 250/339 |
| 4,044,257 | 8/1977 | Kreuzer | 250/344 |
| 4,268,751 | 5/1981 | Fritzlen et al. | 250/343 |
| 4,525,627 | 6/1985 | Krempl et al. | 250/343 |

FOREIGN PATENT DOCUMENTS

| | | | |
|---|---|---|---|
| 0376301 | 3/1984 | Austria . | |
| 2557508 | 7/1976 | Fed. Rep. of Germany | 250/345 |
| 1000070 | 11/1976 | Canada | 250/343 |

Primary Examiner—Janice A. Howell
Assistant Examiner—William F. Rauchholz
Attorney, Agent, or Firm—Watson, Cole, Grindle & Watson

[57] ABSTRACT

In conventional methods of quantitative hydrocarbon analysis in gaseous samples by means of infrared transmission, systematic inaccuracies may be found which are caused by changes in the composition of the components contained in the sample. Such inaccuracies typically amount to 10 to 30% of the measured value, with occasional rises of up to 100%. In order to eliminate this disadvantage the invention proposes that for determining the total mass of gaseous and condensed hydrocarbons radiation be used with a frequency band whose integral infrared absorption has approximately the same value for each of the main hydrocarbons present.

7 Claims, 2 Drawing Sheets

4,771,176

METHOD FOR QUANTITATIVE ANALYSIS OF HYDROCARBON

BACKGROUND OF THE INVENTION

This invention relates to a method for the quantitative analysis of hydrocarbons in gaseous samples, above all in unfiltered exhaust gases, in which the infrared transmission of the electromagnetic radiation penetrating the sample and a reference volume is measured, and the difference in radiation intensities is used as a measured value.

DESCRIPTION OF THE PRIOR ART

An exhaust gas analysis system employing the above method is described in German laid-open print DE-OS No. 2 557 508. In this system infrared radiation with a wavelength of 3 to 5 μm is passed alternatingly through a reference chamber containing a reference gas, and a chamber containing a gaseous sample, e.g., the exhaust gas of a vehicle. The two chambers are provided with filters both on the input and on the output side which will pass radiation of the above wavelength. After passage through the sample chamber or the reference chamber, the infrared radiation is focused on an arrangement of two infrared detectors by means of a concave mirror. In front of each of the infrared detectors an infrared filter is placed, one of which passes a radiation band centered on 4.74 μm, i.e., the point of maximum CO absorption; the other filter for measuring hydrocarbon concentrations passes a radiation band of a wavelength centered on the absorption maximum of the hydrocarbon hexane. Upon evaluation, the electric signals generated by the detectors indicate the concentration of carbon monoxide and that of the hydrocarbon, respectively, relative to the reference chamber. Conventional interference filters used for analyzing hydrocarbon concentrations in a wavelength range of 3.2 to 3.7 μm will only yield gravimetrically correct values for the overall content of hydrocarbons if the relative composition of the hydrocarbon components in the exhaust gas remains practically unchanged. With the use of such interference filters, systematic inaccuries caused by changes in composition may occur, typically of 10 to 30%, and in some cases of up to 100% of the measured value, however.

If the hydrocarbons are to be determined in unfiltered exhaust gases as well, a disturbance variable in quantitative hydrocarbon analysis is constituted by the content of graphitic particles with broad-band absorption, which will vary with the operating parameters of the internal combustion engine. In this context a method is discussed in AT-PS 376 301, in which electromagnetic radiation with wavelengths ranging from 3.8 to 4.15 μm, is passed through an exhaust gas loaded with graphitic particles, especially carbon black, and the particle contents may be inferred from the subsequent decrease in radiation intensity due to absorption. In the above infrared range a disturbance-free result is obtained for graphitic particles since none of the components present in the exhaust gas will contribute to the absorption to be measured; absorption in this frequency range has been found to be exclusively due to the graphitic particles with broad-band absorption.

SUMMARY OF THE INVENTION

It is an object of the present invention to improve a method of the above kind in such a way as to ensure that the quantitative analysis of hydrocarbons in gaseous samples will yield results of high accuracy even if the relative composition of the hydrocarbon components in the exhaust gas to be analyzed should vary considerably.

According to the invention this object is achieved by determining the total mass of gaseous and condensed hydrocarbons present in the gaseous sample by means of electromagnetic radiation of a frequency band whose integral infrared absorption is approximately the same for each of the main hydrocarbons present—preferably electromagnetic radiation with a frequency band of a central wavelength of $3.465 \pm 0.05$ μm, and of a half-band width of 0.07 to 0.18 μm, and a 5% cuton at a wavelength $> 3.35$ μm, and a 5% cutoff at a wavelength $< 3.58$ μm, and by determining, in a conventional manner, the total mass of carbon particles contained in the sample by measuring the transmission of infrared radiation in the range of 3.8 to 4.15 μm, and, furthermore, by employing the value obtained in this context for correction of the value obtained upon measuring the total mass of hydrocarbons. Based on the unexpected finding that the integral infrared absorption of electromagnetic radiation in narrow frequency bands is virtually identical for all hydrocarbons, and that the relative integral infrared absorption of an exhaust gas, e.g., consisting of a mixture of propane, isobutane, n-decane, n-hexadecane, will fluctuate about a mean value by $+1$ to 7% only, with reference to a standard total mass, it will be possible in this wavelength range to accurately determine the total mass of hydrocarbons even in case of considerable variations in the composition of the exhaust gas. The term standard total mass denotes that infrared absorption refers to standard boundary conditions, such as 1 g/m$^3$ mass load of hydrocarbons at 760 torr and 20° C. room temperature.

Frequency bands meeting the above specifications have properties such as central wavelength $3.465 \pm 0.05$ μm, half-band width 0.07 to 0.18 μm, slope widths less than 2% and 2.5%, respectively, of the central wavelength; or central wavelength $3.41 \pm 0.15$ μm, half-band width smaller than 0.07 μm, slope widths less than 0.08% of central wavelength.

By defining a cuton and a cutoff value for the frequency band, i.e., frequency values where a defined intensity relative to the maximum intensity obtained at the central wavelength, is exceeded, another specification is given with regard to the shape of the frequency band, which - if met - will further increase measuring accuracy.

The invention will be better understood by reference to the accompanying drawings, taken in conjunction with the following discussion.

DETAILED DESCRIPTION

Figure 1:
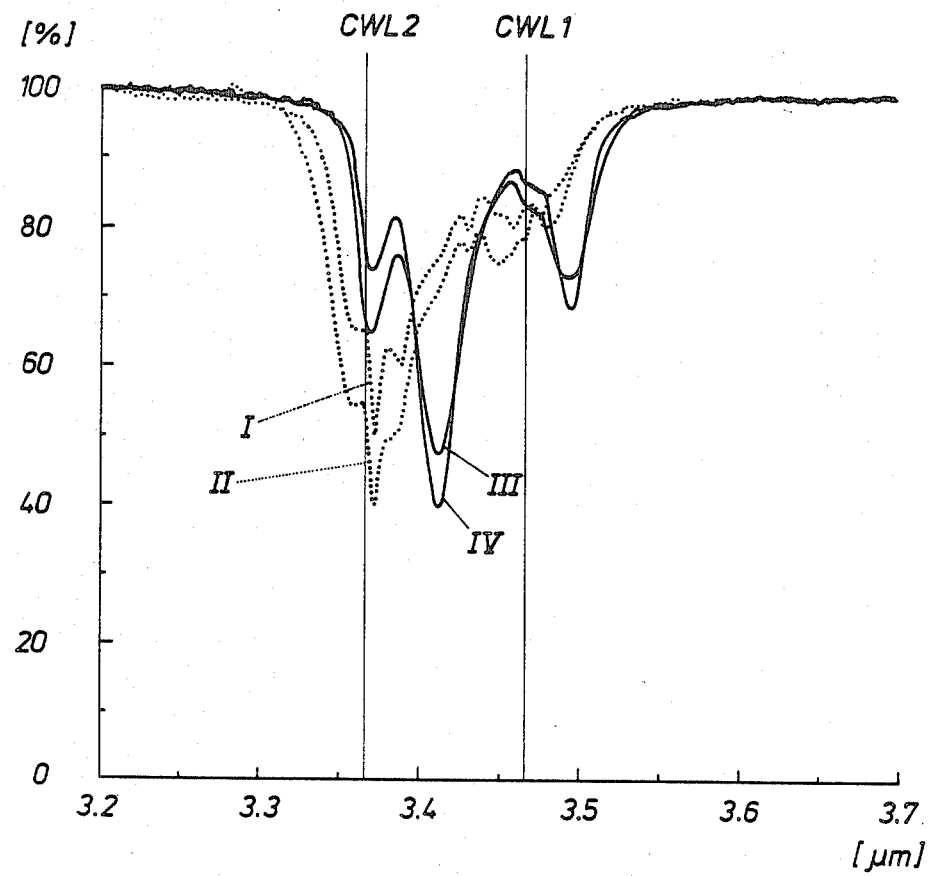
FIG. 1 is a graph showing the infrared spectra of hydrocarbons.

FIG. 1 shows the infrared spectra of hydrocarbons standardized gravimetrically to an identical total mass), the horizontal axis indicating the wavelength in μm and the vertical axis the transmission of radiation in percent. The absorption of infrared radiation of hydrocarbons that are not condensed at 20° C. (e.g., isobutane, propane), represented by curves I and II, and of hydrocarbons that are condensed at 20° C. (e.g., n-decane, n-hexadecane), represented by curves III and IV, shows marked differences in the range of wavelengths under discussion. This is due to the fact that the hydrocarbons which have not been condensed at a given ambient temperature (e.g., 20° C.), usually contain a percentage by volume of $CH_3$ molecules much higher than that of the long-chain hydrocarbons condensed at this ambient temperature. Nevertheless at 3.465 μm for instance, a region marked CWL1 can be observed, in which the individual transmission values of the hydrocarbons are virtually identical when they are integrated over the wavelength interval defined by the frequency band used.

By determining the total mass of carbon particles contained in the sample, which is obtained by measuring the transmission of infrared radiation in the range of 3.8 to 4.15 μm, the contribution of these particles to absorbtion may be determined in the range of wavelengths used for measuring the total mass of cgaseous and condensed hydrocarbons. By subtracting this quantity from the value corresponding to the hydrocarbon content, the latter may be determined with high accuracy.

A preferred variant of the invention provides that the total mass of highly volatile, gaseous hydrocarbons be determined with the additional use of electromagnetic radiation of another frequency band with a central wavelangth of 3.365±0.025 μm, a half-band width <0.1 μm, a 5% cuton at a wavelength of >3.29 μm and a 5% cutoff at a wavelength of >3.45 μm. In addition, FIG. 1 shows that in a region around 3.365 μm, marked CWL2, there are considerable differences between the infrared absorption of non-condensed hydrocarbons (I,II) and that of condensed hydrocarbons (III,IV). By using infrared radiation of the above frequency bands for measuring hydrocarbon concentrations in exhaust gases, with one frequency serving for gravimetric determination of the total mass of all hydrocarbons and the other one giving more weight to hydrocarbons that are gaseous at a room temperature of 20° C. than to those that are at least partly condensed at this temperature, it has become possible to obtain from the two values measured, separate readings for the gravimetric percentages of hydrocarbons in the exhaust gas that are gaseous at room temperature vs. those that are condensed at room temperature. This is an advantage over the conventional systems of hydrocarbon analysis employed so far. By measuring the purely gaseous hydrocarbons in exhaust gas analysis systems at 160° to 200° C., and by the use of conventional condensation calculations, it has further become possible to determine by dynamic-gravimetrical methods the hydrocarbon components of the exhaust gas precipitating as hydrocarbon particles at a certain ambient temperature, for instance at room temperature.

The different readings obtained with the use of two frequency bands with the central wavelengths CWL1 and CWL2 will thus permit calculation of the hydrocarbon components in the exhaust gas which are gaseous at room temperature. Once the gaseous hydrocarbon component has been determined the measured value corresponding to the total mass of gaseous and condensed hydrocarbons contained in the exhaust gas may be further corrected, as measurement inaccuracy is mainly due to a change in the concentration of the short-chain hydrocarbons in the exhaust gas. In this way an even better gravimetric measuring accuracy may be achieved with standard deviations of less than 5 per cent.

Another variant of the invention provides that for generation of the frequency band used for determining the total mass of gaseous and condensed hydrocarbons an interference filter be placed in the path of the electromagnetic radiation whose transmission in a wavelength interval between 3.38 and 3.55 μm will exceed 50% of the maximum transmission, and that for generation of the frequency band used for determining the total mass of highly volatile, gaseous hydrocarbons an interference filter be placed in the path of the electromagnetic radiation whose transmission in a wavelength interval between 3.31 and 3.42 μm will exceed 50% of the maximum transmission. In this way frequency bands of strong asymmetry with respect to their central wavelength may be employed for measurement purposes if their half-width points are within the above limits. The term half-width points denotes those points at which the frequency band exceeds or falls below 50% of its maximum intensity.

The above specifications of the frequency bands necessary for implementing the method discussed here are best met by special interference filters—preferably interference band-pass filters. Transmission curves of filters for hydrocarbon analysis by non-dispersive infrared spectroscopy are shown in FIGS. 2 and 3.

Figure 2:
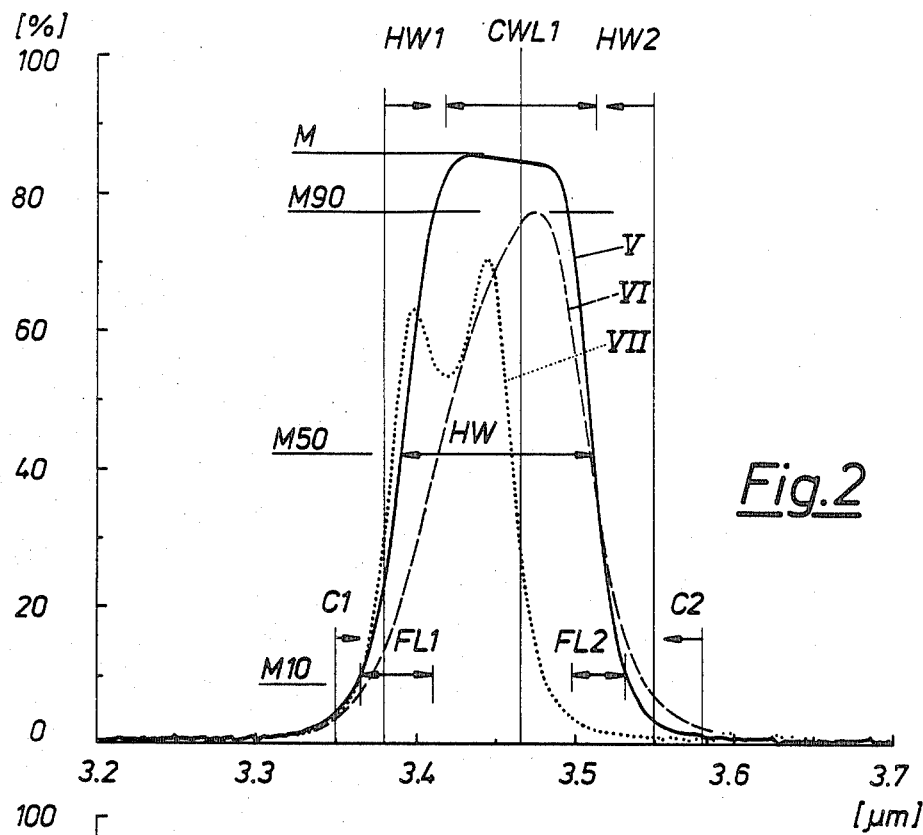
FIGS. 2 and 3 illustrate the characteristics of filters used in the present invention for hydrocarbon analysis.

FIG. 2 shows the transmission curves V, VI, VII of three filters, each of which may be used individually for measuring the total mass of gaseous and condensed hydrocarbons. The parameters of the interference filters suitable for gravimetric measurement are the following: the central wavelength CWL1 is situated at 3.465±0.05 μm, with a half-band width HW of 0.07 to 0.18 μm, taken at 50% M 50 of the maximum intensity M. The half-width points HW1 and HW2 should be >3.38 and >3.55 μm, respectively. Slope steepness of the transmission curves is indicated in FIG. 2 by a rise from 10 to 90% of the maximum intensity M, marked M 10 and M 90, within a wavelength interval FL1, or by a decline within a wavelength interval FL2. The 5% cuton C1 is at values >3.35 μm; the 5% cutoff C2 at values >3.58 μm.

Figure 3:
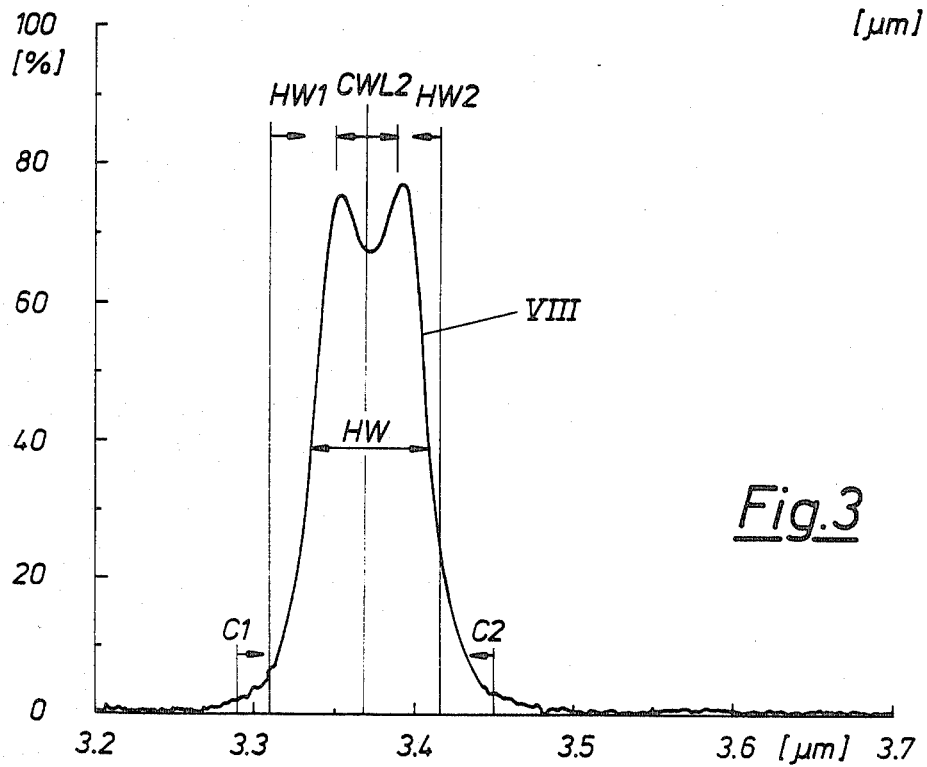

The interference filter represented in FIG. 3 by its transmission curve VIII is used for measurement of the highly volatile, gaseous hydrocarbons. The central wavelength CWL2 should be in a range of 3.365±0.025 μm, and the half-band width HW should be >0.1 μm. For the remaining parameters the following will apply: half-width points HW1 >3.29 μm, HW2 <3.45 μm, rise of the transmission curve from 10 to 90% of maximum intensity within a range <1.5% of the central wavelength, identical slope steepness at the long-wave end of the curve, 5% cuton >3.29 μm and 5% cutoff <3.45 μm.

The use of three interference filters, one of them for conventional gravimetric measurement of the graphitic particles of the exhaust gas, and the other two for determining the hydrocarbons in the exhaust gas in accordance with the invention, will permit to measure at one and the same time, by a dynamic-gravimetric method, the total mass of hydrocarbons, the overall particle mass precipitating at a given ambient temperature, for example 20° C., the mass of graphitic particles, the mass of condensed hydrocarbon particles present at this temperature, and the mass of non-condensed, gaseous hydrocarbons in an exhaust gas. For joint measurement of these data multiple measuring devices have been required up to now whose measuring systems partly are based on different physical principles.

Besides, it has not been possible so far, to perform dynamic measurements on all these values with a time resolution of better than 0.2 secs, especially if particle contents had to be measured at the same time.

An enhanced version of the invention provides that the transmission of the interference filters outside their pass-band in a wavelength range from 10 μm up to the visual range should be less than 0.1% of the maximum transmission in the range of the respective central wavelength. This further characteristic of the interference filters used by the method according to the invention refers to the transmission of these filters outside the frequency range used for measurement purposes. The "blocking" value outside the measuring range should not exceed 0.1% of the maximum intensity at the central wavelength. This is shown clearly in FIGS. 2 and 3, were transmission intensity both in the short-wave and in the long-wave range rapidly drops to very small values.

Finally, the invention provides that one or more narrow-band emitting infrared sources, e.g., lasers, be used for generating the frequency bands required.

We claim:

1. A method for determining the total mass of gaseous and condensed hydrocarbons in a gaseous sample which contains gaseous hydrocarbons, condensed hydrocarbons and carbon particles, said method comprising the steps of
   (1) passing electromagnetic radiation having a frequency band whose central wavelength is 3,465±0.05 μm, whose half-band width is 0.07 to 0.18 μm, whose 5% cuton is at a wavelength >3.35 μm and whose 5% cutoff is at a wavelength of <3.58 μm through said gaseous sample and through a reference volume,
   (2) measuring the intensity values of the electromagnetic radiation after passing through said gaseous sample and said reference volume in step (1),
   (3) determining the difference in intensity values measured in step (2) to provide a preliminary value of the total mass of gaseous and condensed hydrocarbons.
   (4) passing electromagnetic radiation having a wavelength of 3.8 to 4.15 μm through said gaseous sample and said reference volume,
   (5) measuring the intensity of the elelctromagnetic radiation after passing through said gaseous sample and said reference volume in step (4),
   (6) determining the difference in intensity values determined in step (B 5) to provide a value of the total mass of carbon particles in said gaseous sample, and
   (7) correcting the value obtained in step (3) with the value obtained in step (6).

2. A method according to claim 1, comprising the additional steps of
   (1) passing electromagnetic radiation having a frequency band whose wavelength is 3,365±0.025 μm, whose half-band width is <0.1 μm, whose 5% cuton is at a wavelength >3.29 μm and whose 5% cutoff is at a wavelength <3.45 μm through said gaseous sample and through said reference volume,
   (9) measuring the intensity values of the electromagnetic radiation after passing through said gaseous sample and said reference volume in step (8),
   (10) determining the difference in intensity values determined in step (9), and
   (11) computing a value of the total mass of gaseous hydrocarbons with values obtained in steps (7) and (10).

3. A method according to claim 2, wherein said electromagnetic radiations in steps (1) and (8) are provided by lasers.

4. A method according to claim 2, wherein said electromagnetic radiation in step (1) is provided by passing broad-band electromagnetic radiation through an interference filter whose transmission in a wavelength interval between 3.38 and 3.55 μm will exceed 50% of the maximum transmission.

5. A method according to claim 2, wherein said electromagnetic radiation in step (8) is provided by passing broad-band electromagnetic radiation through an interference filter whose transmission in a wavelength interval between 3.31 and 3.42 μm will exceed 50% of the maximum transmission.

6. A method according to claim 1, wherein said electromagnetic radiation in step (1) is provided by passing broad-band electromagnetic radiation through an interference filter whose transmission in a wavelength interval between 3.38 and 3.55 μm will exceed 50% of the maximum transmission.

7. A method according to any of claims 3 to 5, wherein the transmission of said interference filters outside their pass-band in a wavelength range from 10 μm up to the visual range is less than 0.1% of the maximum transmission in the range of said respective central wavelength.

* * * * *

UNITED STATES PATENT AND TRADEMARK OFFICE
CERTIFICATE OF CORRECTION

PATENT NO. : 4,771,176

DATED : September 13, 1988

INVENTOR(S) : Erich J. Schiefer et al.

It is certified that error appears in the above-identified patent and that said Letters Patent is hereby corrected as shown below: On the title page assignee should read -- [73] Assignee: AVL GESELLSCHAFT FÜR VERBRENNUNGSKRAFTMASCHINEN UND MESSTECHNIK M.B.H., Prof.Dr.Dr.h.c. Hans List --.

Signed and Sealed this

Seventeenth Day of January, 1989

Attest:

DONALD J. QUIGG

Attesting Officer

Commissioner of Patents and Trademarks